United States Patent
Garrison

(10) Patent No.: US 7,785,885 B2
(45) Date of Patent: Aug. 31, 2010

(54) RESCUE OF PLANT CELL CULTURES AND SUSPENSIONS AFTER CRYOPRESERVATION-INDUCED DAMAGE

(75) Inventor: Robbi J. Garrison, Fillmore, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 297 days.

(21) Appl. No.: 12/173,075

(22) Filed: Jul. 15, 2008

(65) Prior Publication Data

US 2009/0023214 A1    Jan. 22, 2009

Related U.S. Application Data

(60) Provisional application No. 60/950,471, filed on Jul. 18, 2007.

(51) Int. Cl.
*C12N 5/00* (2006.01)
*C12N 15/00* (2006.01)
*A01N 1/00* (2006.01)
*C12P 21/06* (2006.01)
*C07K 14/00* (2006.01)
*A61K 45/00* (2006.01)

(52) U.S. Cl. .............. 435/430; 435/2; 435/68; 435/811; 435/320; 530/351; 424/85; 424/85.2

(58) Field of Classification Search ............ 435/1.3, 435/2, 374, 422, 1.1, 68, 811, 320; 424/85, 424/85.2; 530/351
See application file for complete search history.

(56) References Cited

U.S. PATENT DOCUMENTS 5,965,438 A * 10/1999 Kadkade et al. .......... 435/420
6,596,531 B2 * 7/2003 Campbell et al. ........... 435/260
6,682,931 B2 * 1/2004 Becwar et al. .............. 435/422
6,783,984 B2 * 8/2004 Florin et al. ............. 435/430.1
2005/0026282 A1 * 2/2005 Gupta et al. ............... 435/419

FOREIGN PATENT DOCUMENTS

| EP | 0 573 767 A | 12/1993 |
|---|---|---|
| EP | 1 359 220 A | 11/2003 |
| WO | WO 96/39812 A | 12/1996 |

OTHER PUBLICATIONS

Sarkar et al. Caspase-mediated apoptosis and cell death of rhesus macaque CD4+ T-cells due to cryopreservation of peripheral blood mononuclear cells can be rescued by cytokine treatment after thawing. Academic Press. (2003), Cryobiology 47 44-58.*

Sarkar Surojit et al., "Caspase-mediated apoptosis and cell death of rhesus macaque CD4+ T-cells . . . after thawing," Cryobiology, vol. 47, No. 1, pp. 44-58, 2003, [Abstract only].

Anthony P et al., "Pluronic F-68 increases the post-thaw growth of cryopreserved plant cells," Cryobiology, vol. 33, No. 5, pp. 508-514, 1996, [Abstract only].

Desai nina et al., "Assessment of growth factor effects on post-thaw . . . to the blastocyst stage," Human Reproduction, vol. 15, No. 2, pp. 410-418, 2000.

Mori Masahi et al., "mRNA amplification system by viral replicase in transgenic plants," FEBS Letters, vol. 336, No. 1, pp. 171-174, 1993.

* cited by examiner

*Primary Examiner*—Annette H Para
(74) *Attorney, Agent, or Firm*—Ronald S. Maciak

(57) ABSTRACT

The subject invention relates to recovery of cryopreserved plant cell cultures after cryopreservation. The use of canine IL-4 and human gamma interferon is exemplified in some preferred embodiments.

5 Claims, 1 Drawing Sheet

Samples: (1) non-frozen cells; (2) cells immediately after thaw; (3) cells 24 hours post thaw; (4) cells 48 hours post thaw

RESCUE OF PLANT CELL CULTURES AND SUSPENSIONS AFTER CRYOPRESERVATION-INDUCED DAMAGE

BACKGROUND OF THE INVENTION

Routine maintenance of cell suspensions by repeated weekly subculture is labor intensive and creates cell cultures that change over time. Cryopreservation of cells addresses some of these issues. For example, U.S. Pat. Nos. 5,965,438; 6,127,181; and 6,753,182 relate to some techniques for cryopreservation of plant cells.

Sarkar et al. (*Cryobiology* 47 [2003] 44-58) relates to defining mechanistic pathways involved in cryopreservation-induced damage of CD4+ T-cells, and to evaluating a cytokine treatment of the cryopreserved samples to rescue apoptosis for the potential future use of the cryopreserved peripheral blood mononuclear cells (PBMC). Using cryopreserved PBMC samples isolated from naïve and Simian immunodeficiency virus (SIV)-infected rhesus macaques, Sarkar et al. report that frozen PBMC showed significantly increased levels of apoptosis-induced CD4+ T-cell death compared to fresh PBMC over a 5-day culture period. Sarkar et al. report that mechanistic studies using a broad-spectrum caspase inhibitor (z-VAD) demonstrated an involvement of caspases in cryopreservation-induced apoptosis of CD4+ T-cells. Sarkar et al. evaluated the ability of a combined IL-2, IL-4, and IL-7 cytokine treatment of the cryopreserved cells to rescue apoptosis of the CD4+ T-cells. Sarkar et al. reported that efficient rescue of cryopreserved CD4+ T-cells has clinical significance in immune function analysis of longitudinal samples and in various long-term protocols requiring cryopreservation, including bone marrow and stem cell transplantation.

In an effort to reduce labor as well as culture variation, cryopreservation of non-transformed and transformed plant cultures and master seed stocks were developed and optimized as described in WO 2006/052835 and US 2006-0101539. A master seed stock may be utilized as a primary source of starting material for the generation of transgenic product or as a primary starting source of transformed plant cells for manufacturing biopharmaceuticals. Consistent recover of plant cultures and master seed stocks over time often deteriorates and may result in no actively growing cells from the master seed stock. Even thought immediate post thaw viability may be excellent as visualized with FDA stain, 24 hours post thaw cultures often show substantial DNA degradation accompanied by damage and cell death.

To date, there has been no illustration of techniques for rescuing plant cell cultures and master seed stocks from cryopreservation-induced damage.

BRIEF SUMMARY OF THE INVENTION

The subject invention relates to recovery and rescue of cryopreserved plant cell cultures after cryopreservation that would otherwise fail to reproducibly recover and thrive. The use of canine IL-4 and human gamma interferon in the method is exemplified.

DETAILED DESCRIPTION OF THE INVENTION

Figure 1:
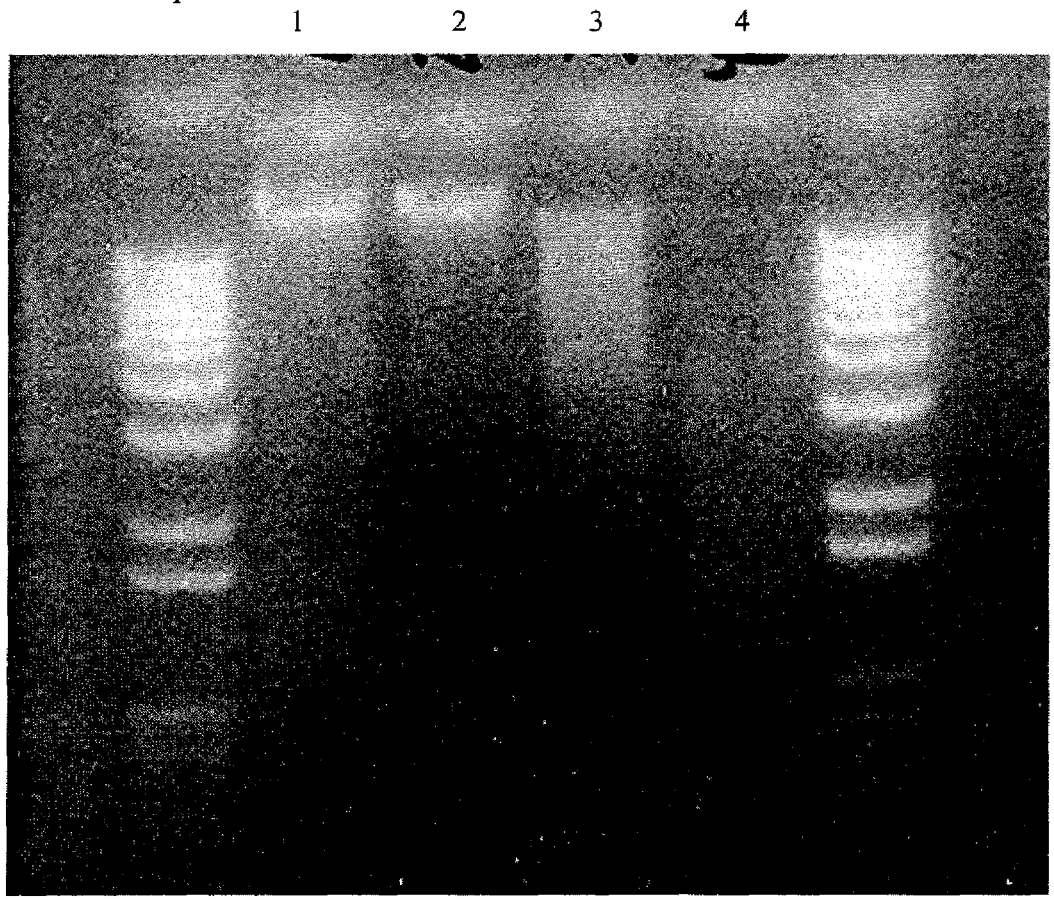
FIG. 1 shows that DNA degradation normally seen during death of cells was observed within 24 hours of thawing. Samples/lanes: (1) non-frozen cells; (2) cells immediately after thaw; (3) cells 24 hours post thaw; and (4) cells 48 hours post thaw.

Canine IL-4 (interleukin-4) as used herein is described in detail in U.S. Pat. No. RE 39,614 (incorporated by reference in its entirety).

Human IFN-γ (interferon gamma) as used herein is described in detail in U.S. Pat. No. 4,758,656 (incorporated by reference in its entirety), as well as in Gray, P. W. and Goeddel, D. V. (1982). "Structure of the human immune interferon gene". *Nature* 298: 859-863.

The subject invention relates to recovery of cryopreserved plant cell cultures and master seed after cryopreservation-induced programmed cell death. The subject invention relates in part to inhibition of cryopreservation-induced damage by using canine IL-4. In another example, human IFN-γ was successfully used, as well. Thus, the subject invention relates in part to the use of human IFN-γ for rescuing plant cell cultures from cryopreservation-induced damage.

Methods of the subject invention can be applied to recovery of cryopreserved plant cells, generally. Thus, the subject invention includes recovery of cryopreserved monocots and dicots (monocotyledonous cells and dicotyledonous cells). Methods of the subject invention can also be used for recovery of any plant cell line (tobacco or otherwise) from cryopreservation, and recovery of any plant tissue from cryopreservation. Preferred plant cell cultures for practicing the claimed methods include cultures derived from monocots and dicots. Another group of preferred plant cell cultures are derived from tobacco, rice, carrot, corn, rape and cotton plants. A preferred sub-group is derived from tobacco and rice Of the sub-group, a preferred group is T309 rice cultures, BY-2 and NT-1 tobacco cell cultures (See "Tobacco BY-2 Cells"; Edited by Nagata, Toshiyuki; Hasezawa, Seiichiro; Inzé, Dirk; Springer, 2004).

The present invention relates in part to methods of recovering transformed and non-transformed cells from cryopreservation. Cultures of cells that have been successfully recovered from cryopreservation are also provided. The recovered cells can be used to re-establish growing cell cultures that retain the genotype and phenotype of the original cryopreserved culture.

One example herein is the demonstration of "rescue" of cryopreserved tobacco BY-2 suspension master seed after cryopreservation-induced programmed cell death. In some preferred embodiments, canine IL-4-secreting rice cultures are used. To facilitate recovery of the tobacco culture discussed above in the Background section, the incorporation of spent media and/or a feeder layer, from a transgenic rice event producing canine IL-4, overlaying standard recovery media plates produced full recovery after 5 to 14 days post thaw.

The subject invention also provides for genetic and product stability of target gene(s) or gene product(s) after prolonged storage and/or cultivation after removal from storage, both from a primary Master Seed Stock and an expanded and re-cryopreserved Working Seed Stock. "Master Seed principles" for biopharmaceutical and bioagrochemical production typically involve the use of live organisms in manufacturing procedures and the preservation of a single culture of defined origin and passage history with defined characteristics of cell phenotype and desired features. For a master seed, preservation (typically cryopreservation) is typically long lasting (spanning several years or more); the cell can be recovered, expanded, passaged indefinitely into "working seed" and subjected to another period of cryopreservation (a principle that requires robustness of the cell); and the cell does not lose the defined characteristics of cell phenotype and desired manufacturing features found prior to the initial cryo-state after a defined number of passages.

The term "passaging" is akin to "short cycle condition(s)." Passaging or short cycle conditions typically involve harvesting (withdrawing) cells during mid-exponential (mid-log) growth, diluting or splitting the cells at mid-exponential growth with fresh culture media, and cultivating the diluted (split) cell culture to mid-exponential growth. The terms "mid-log" and "mid-exponential" as used herein do not necessarily refer to the precise mid-point of exponential growth but rather to a range around the mathematical mid-point. Each round of cultivation to mid-exponential growth is considered one cell passage. Cells to be cryopreserved from suspension can be successfully cryopreserved with only 1 short-cycle (passage) or up to as many as about 20 short cycles. About three to six short cycles are generally preferred, and about 6 short cycles are typically more preferred. 6 short cycles (passages) allows for exceptional recovery of cells from a cryopreserved state for recultivation. Additionally, cells can be cryopreserved multiple times after cultivation if cells are placed in suspension under short cycle conditions about 1-6 times.

Various techniques for cryopreserving plant cells are known in the art. See e.g. U.S. Pat. Nos. 5,965,438; 6,127, 181; and 6,753,182. WO 2006/052835 and US 2006-0101539 relate to cryopreservation of plant cells and features needed for use of a biological agent in a biopharmaceutical manufacturing environment. Techniques devised for prolonged storage of viable biological agents should preferably provide biological agents that are stable over long periods of times (years); the storage conditions should not alter the biological agent needed for the manufacturing process; and the agent should be readily available for regrowth once removed from storage and expandable into working seed that can be regrown. WO 2006/052835 and US 2006-0101539 provide information related to lengths of cryopreservation (often measured in months or even hours) and to nearly indefinite growth of cells, or at least to a desired number of passages under normal culture conditions.

Thus, the subject invention provides, in part, methods for the recovery of transformed plant cells from cryopreservation, optionally under master seed principles. In certain embodiments of the subject invention, the methods are applied to methods for cryopreservation of Nicotina tabacum (NT-1 and BY-2) cells and T309 rice cells under master seed principles. See Biotechnology in Agriculture and Forestry, Eds. T. Nagata, S. Hasezawa, and D. Inze; Springer-Verlag; Heidelberg, Germany; 2004.

The T309 rice cell line exemplified herein was prepared from commercially available rice T309 variety using standard plant tissue culture techniques. Additional transformed and untransformed plant cells that are suitable for the practice of the subject invention are provided in Table 1.

Unless specifically indicated or implied, the terms "a", "an", and "the" signify "at least one" as used herein.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLES

Example 1

Plant Cell Cultures

The BY-2 cell suspension cultures were maintained according to the standard methods (See "Tobacco BY-2 Cells"; Edited by Nagata, Toshiyuki; Hasezawa, Seiichiro; Inzé, Dirk; Springer. 2004) on a 7 day subculture schedule.

Non-transgenic T309 rice suspensions and transgenic T309 rice suspensions expressing canine IL-4 targeted for secretion, were maintained by sub-culturing every 7 days in AA cell culture media [PhytoTechnology stock # PhytoTech CM024, plus 20 g/L sucrose] by placing 3 pack cell volume of cells into 50 ml of new media in a 250 ml flask at 28° C. on a rotary shaker at 125 RPM.

Spent media from these suspensions was collected on day 7 alter subculture and filter sterilized with a Steriflip 0.22 μm filter unit [Millipore #SE1M179M6].

Example 2

Maintenance of Tobacco BY-2 Suspension Cultures

The cultures were maintained at 25° C. (130 RPM) with a 7-day subculture schedule. To subculture, 0.125 ml packed cell volume (PCV) of tobacco cells (measured with a 1 ml pipet) are added to 25 ml LS-BY2+B15 (15 mg/L Bialaphos) medium in 125 ml flasks.

For scale up, the number of flasks was either increased per line, or subcultures were moved to a larger flask as follows:

| Flask Size | PCV cells (ml) Packed Cell Volume | Size of pipet to Measure PCV | Media Volume (ml) |
|---|---|---|---|
| 125 ml | 0.125 ml | 1 ml | 25 ml |
| 250 ml | 0.25 ml | 1 ml | 50 ml |
| 500 ml | 0.5 ml | 2 ml | 100 ml |

For non-transgenic tobacco cultures, the same schedule and tissue amounts were used, but LS-BY2 Liquid (which has no selection agent) was used.

Example 3

Cryopreservation of BY-2 Tobacco Suspensions—7 Day Cycle

The protocol used was adapted from a standard embryogenic maize suspension protocol (See Petolino, Welter. Cai: Molecular Methods of Plant Analysis, Vol. 23, chapter 9) which utilized a 1 hour pre-treatment at 4° C. in a cryoprotectant solution consisting of 2 M sucrose, 1 M glycerol and 1 M DMSO in a MS cell culture media containing 2.5 M Proline.

The suspensions were maintained by sub-culturing every 7 days in LS cell culture media containing LS basal salts (PhytoTechnology Labs L689), 170 mg/L K2HP04, 30 g/L sucrose, 200 ul of 1 mg/ml 2,4D, 0.6 mg/L Thiamine-HCL, in a 250 ml flasks with total volume of 50.5 ml [0.5 ml cell suspension+50 ml new media] maintained on a rotary shaker at 28 C and 125 RPM.

5 days after sub-culturing, the entire flask of suspension was pipetted into a sterile 50 ml centrifuge tube, left to settle for 5 min and supernatant discarded using a pipette (done at room temperature). The supernatant above the cell mass was removed and additional media was added by pipetting from the bottom of the centrifuge tube (through the cell pellet). Care was taken to not to disturb the cell pellet, as much medium was taken off as possible. The packed cell volume was measure by using the markings on the centrifuge tube. An equal volume of room temperature BY-2+VP medium (containing MS basal salts, MS vitamins, 100 mg/L myo-inositol, 170 mg/L KH2PO4, 200 ul of 1 mg/ml 2,4-D, 30 g/L sucrose and 2.4 ml/L of 2.5M L-proline) was added equivalent to the packed cell volume; mixed and transferred into sterile 125 ml flasks then equal volume of cryoprotectant was added.

Cells with cryoprotectant were placed on a rotary shaker at 4° C. and 125 RPM for a one-hour pretreatment. After pretreatment 2.5 ml aliquots of cell/cryoprotectant mix were placed in chilled, sterile 4 ml coming cryo-vials (Fisher catalog #976174) using a repeat pipetter.

Filled vials were placed in a model 7452 ThermoForma Cryomed controlled rate freezer pre-chilled to 4° C. Vials were maintained at 4° C. for 15 minutes then cooled at a rate of 0.5° C. per minute to a temperature of −40° C. Vials were then moved to a ThermoForma CryoPluS™ 4 liquid nitrogen, vapor phase storage unit.

Example 4

Cryopreservation of BY-2 Tobacco Suspensions-3.5 Day Cycle

The protocol used was adapted from a standard embryogenic maize suspension protocol (See Petolino, Welter. Cai: Molecular Methods of Plant Analysis, Vol. 23, chapter 9) which utilizes a 1 hour pre-treatment at 4 C in a cryoprotectant solution consisting of 2 M sucrose, 1 M glycerol and 1 M DMSO in a MS cell culture media containing 2.5M Proline.

The suspensions were maintained by sub-culturing every 3.5 days in LS cell culture media containing LS basal salts (PhytoTechnology Labs L689), 170 mg/L K2HP04, 30 g/L sucrose, 200 ul of 1 mg/ml 2,4D, 0.6 mg/L Thiamine-HCL, in 500 ml flasks with total volume of 120 ml [Diluted with 80 mls new media, sub 40 mls of dispersed suspension into 80 mls of new media] maintained on a rotary shaker at 28° C. and 125 RPM.

2 days after sub-culturing, the entire flask of suspension was pipetted/poured into a sterile 500 ml centrifuge bottle, left to settle for 5 min and supernatant discarded using a pipette (done at room temperature). After removing supernatant, additional media was remove by pipetting from the bottom of the centrifuge tube (through the cell pellet). Care was taken to not to disturb the cell pellet and to take off as much medium as possible. The packed cell volume was measure by using the markings on the centrifuge bottle. An equal volume of room temperature BY2+VP medium (containing MS basal salts, MS vitamins, 100 mg/L myo-inositol, 170 mg/L KH2PO4, 200 ul of 1 mg/ml 2,4-D, 30 g/L sucrose and 2.4 ml/L of 2.5M L-proline) was added equivalent to the packed cell volume, mixed and 10 mls were transferred into each sterile 125 ml flasks then equal volume of cryoprotectant was added.

Cells with cryoprotectant were then placed on a rotary shaker at 4° C. and 125 RPM for the one-hour pretreatment. After pretreatment 2.5 ml aliquots of cell/cryoprotectant mix were placed in chilled, sterile 4 ml coming cryo-vials (Fisher catalog #976174) using a repeat pipetter.

Filled vials were placed in a model 7452 ThermoForma Cryomed controlled rate freezer pre-chilled to 4° C. Vials were maintained at 4° C. for 15 minutes then cooled at a rate of 0.5° C. per minute to a temperature of −40° C. Vials were then moved to a ThermoForma CryoPluS™ 4 liquid nitrogen, vapor phase storage unit.

Example 5

Thawing of Cryopreserved Tobacco Cells

Vials were removed from the storage unit and placed on dry ice, then placed in a rack inside a 45° C. pre-heated water bath. The rack with vials was gently agitated in the bath to help facilitate rapid uniform thawing of the vials. After ~2.5 minutes, vials were gently inverted to mix cells. Inside a laminar flow hood, tubes were pooled and 2 ml of cells were pipetted onto stacks of 8-10, sterile 70 mm #4 Whatman filter papers in sterile petri dishes, covered and allowed to drain for 2 minutes. After draining, the top filter with cells was transferred to semisolid recovery media (see Table 1 for recovery media variations).

The media plate with cells was then incubated in the dark at 28° C. Cell growth was scored between 5 and 14 days. For treating the cells with various additives, a feeder layer of transgenic rice suspension or other additive was pipetted onto LSBY2 semisolid recovery media before placing the filter containing thawed BY-2 cells on the plate. Controls were standard semisolid LSBY2 media with no overlay additions and LSBY2 semisolid with liquid rice AA maintenance media and liquid LSBY2-VP tobacco maintenance media overlay. Evaluation of DNA post thaw was done by lyophilizing cell samples at 4° C. and extracting DNA with the Qiagen DNeasy™ Kit (Qiagen #69506). A total of 250 ng DNA was loaded on a 1% agarose gel and stained with ethidium bromide.

Example 6

Successful Recovery

Originally, monitoring of recovery of cryopreserved BY-2 master seed demonstrated that the cells lost viability. Although the cells were viable immediately after thawing, they died within 24 hours. DNA degradation normally seen during cell death was observed within 24 hours of thawing.

Both rice and tobacco cell suspension lines that expressed canine IL-4 were available and were tested. Initial experiments done with either a feeder layer of rice cells expressing IL-4 or spent media from the culture markedly improved recovery (Table 1). The observed rescue of apoptosic cells from cryopreservation was not attributable to the media or any non-specific effects of T-309 rice cells. Only one transgenic rice line was effective in cryopreservation rescue, which was due to differences in expression of IL-4 in that line. Additional evidence for an IL-4 specific effect was demonstrated using transgenic IL-4 producing tobacco cells as a feeder layer. While there might have been a slight improvement in recovery using non-transgenic tobacco cells, a much stronger rescue response was found using the IL-4 expressing cells.

TABLE 1

Rescue of BY2 freeze from cryopreservation

| | | Recovery |
|---|---|---|
| First Experiment | | |
| 1 | overlay recovery media with 3 ml IL-4 expressing rice spent media event #100 day 7 | full at 5 days |
| 2 | feeder layer 3 ml IL4 expressing rice suspension event #100 at day 7 | full at 7 days |
| 3 | control [standard LSBY2 solid] | no growth |
| Second Experiment | | |
| | | observed day 13 due to holiday |
| 1 | overlay recovery media with 3 ml AA rice maintenance media | no growth |
| 2 | overlay recovery media with 3 ml LSBY2-VP2 non-transgenic tobacco maintenance media | no growth |
| 3 | overlay recovery media with 3 ml spent media non-transgenic T309 rice day 7 | no growth |
| 4 | overlay recovery media with 3 ml IL-4 expressing rice spent media event #100 day 7 | spotty growth |
| 5 | overlay recovery media with 3 ml IL-4 expressing rice spent media event #169 day 7 | no growth |
| 6 | overlay recovery media with 3 ml IL-4 expressing rice spent media event #315 day 7 | no growth |
| Third Experiment | | |
| 1 | overlay recovery media with 3 ml IL-4 expressing rice spent media event #100 day 7 | full at 5 days |
| 2 | overlay recovery media with 3 ml IL-4 expressing tobacco feeder layer | full at 9 days |
| 3 | overlay recovery media with 3 ml BY2 tobacco feeder layer | spotty at 9 days |
| 4 | Recovery media without Ca and Mg | no growth |
| 5 | Recovery media without Ca and Mg + 5 mM ZnSO4 | no growth |
| 6 | control [standard LSBY2 solid] | no growth |

Example 7

Use of Human Interferon-gamma (IFN-γ) for Recovery from Cryopreservation

Using methodology similar to that described above for IL-4, human IFN-Y was also successfully used to rescue BY-2 tobacco cell cultures from cryopreservation. Results are summarized in Tables 2 and 3.

TABLE 2

| Treatment | # of plates/ results | Comments |
|---|---|---|
| overlay recovery media with 3 mls IL-4 expressing rice spent media event #100 day 7 (FRESH) | 0/2 | |
| overlay recovery media with 3 mls non-transgenic rice spent media + 0.5 ng interferon-human gamma | 1/2 spotty | |
| overlay recovery media with 3 mls non-transgenic rice spent media + 5 ng interferon-human gamma | 1/2 spotty | |
| overlay recovery media with 3 mls non-transgenic rice spent media + 50 ng interferon-human gamma | 2/2 spotty | 2/2 Full/Half Plate |
| overlay recovery media with 3 mls fresh AA rice media + 0.5 ng interferon-human gamma | 0/2 | |
| overlay recovery media with 3 mls fresh AA rice media + 5 ng interferon-human gamma | 0/2 | |
| overlay recovery media with 3 mls fresh AA rice media + 50 ng interferon-human gamma | 0/2 | |
| overlay recovery media with 3 mls LSBY2 Liquid + 0.5 ng interferon-human gamma | 1/2 [1 spot] | |
| overlay recovery media with 3 mls LSBY2 Liquid + 5 ng interferon-human gamma | 0/2 | |
| overlay recovery media with 3 mls LSBY2 Liquid + 50 ng interferon-human gamma | 0/2 | |
| | 20 plates | |

TABLE 3

| Date | Treatment #1 | Rec. | Treatment #2 | Rec. | Treatment #3 | Rec. | Treatment #4 | Rec. | Treatment #5 | Rec. | Treatment #6 | Rec. |
|---|---|---|---|---|---|---|---|---|---|---|---|---|
| Day 0 | Spent media event #100 rice IL-4 secreted | YES | Control LSBY2 solid media | NO | Feeder layer event #100 rice IL-4 secreted | YES | | | | | | |
| Day 6 | Spent media event #100 rice IL-4 secreted | YES | Control LSBY2 solid media | NO | AA rice media, LSBY2 tobacco media, Spent media non-transgenic rice | NO | Spent media event #169 and event #315 rice IL-4 secreted | NO | Spent media event #169 and event #315 rice IL-4 secreted | NO | Spent media event #169 and event #315 rice IL-4 secreted | NO |
| Day 26 | Spent media event #100 rice IL-4 secreted | YES | Control LSBY2 solid media | NO | Transgenic tobacco feeder layer IL-4 retained | YES | BY2 non-transgenic feeder layer | YES | | | | |

TABLE 3-continued

| Date | Treatment #1 | Rec. | Treatment #2 | Rec. | Treatment #3 | Rec. | Treatment #4 | Rec. | Treatment #5 | Rec. | Treatment #6 | Rec. |
|---|---|---|---|---|---|---|---|---|---|---|---|---|
| Day 33 | Spent media event #100 rice IL-4 secreted | YES | Control LSBY2 solid media | NO | | | | | | | | |
| Day 98 | Spent media event #100 rice IL-4 secreted | NO | Control LSBY2 solid media | NO | Human IL-4 spiked into spent non-transgenic rice media 0.5 ng, 5 ng, 50 ng/ml | NO | Canine IL-4 spiked into spent non-transgenic rice media 0.5 ng, 5 ng, 50 ng/ml | YES | Human interferon-γ spiked into spent non-transgenic rice media 0.5 ng, 5 ng, 50 ng/ml | YES | All 3 treatments [Human IL4, canine IL4, Human interferon-γ] spiked into AA rice media and LSBY2 tobacco media | NO |

The invention claimed is:

1. A method for rescuing plant cells from cryopreservation-induced damage, said method comprising thawing cryopreserved plant cells to obtain thawed cells, and incubating said thawed cells with a recovery agent selected from the group consisting of canine IL-4 and human gamma interferon.

2. The method of claim 1, wherein said thawed cells are grown on a media plate with a feeder layer of transgenic cells that produce said recovery agent.

3. The method of claim 1, wherein said thawed cells are grown on a media plate with spent media produced by transgenic cells that produce said recovery agent.

4. The method of claim 1, wherein the recovery agent is spiked into spent plant cell culture medium.

5. The method of claim 2, wherein said transgenic cells producing said recovery agent are rice cells in a suspension.

* * * * *